（12） United States Patent
Liu et al.

(10) Patent No.: US 7,172,899 B2
(45) Date of Patent: Feb. 6, 2007

(54) METHODS TO CULTURE CIRCOVIRUS (75) Inventors: Qiang Liu, Saskatoon (CA); Suresh K. Tikoo, Saskatoon (CA); Philip Willson, Saskatoon (CA); Lorne A. Babiuk, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 50 days.

(21) Appl. No.: 10/840,879

(22) Filed: May 7, 2004

(65) Prior Publication Data

US 2005/0239187 A1     Oct. 27, 2005

Related U.S. Application Data

(62) Division of application No. 10/112,540, filed on Mar. 27, 2002, now Pat. No. 6,794,163.

(60) Provisional application No. 60/279,173, filed on Mar. 27, 2001.

(51) Int. Cl.
*C12N 5/00*     (2006.01)
*A61K 39/12*    (2006.01)

(52) U.S. Cl. .................... 435/325; 435/69.1; 435/70.1; 424/233.1

(58) Field of Classification Search ............... 435/70.1, 435/71.1, 69.1, 325
See application file for complete search history.

(56) References Cited

U.S. PATENT DOCUMENTS

| | | |
|---|---|---|
| 6,217,883 B1 | 4/2001 | Allan et al. |
| 6,287,856 B1 | 9/2001 | Poet et al. |
| 6,368,601 B1 | 4/2002 | Allan et al. |
| 6,391,314 B1 | 5/2002 | Allan et al. |
| 6,492,343 B1 | 12/2002 | Reddy et al. |
| 6,660,272 B2 | 12/2003 | Allan et al. |
| 6,703,023 B1 | 3/2004 | Jestin et al. |
| 6,794,163 B2 | 9/2004 | Liu et al. |
| 6,943,152 B1 | 9/2005 | Audonnet et al. |
| 2002/0177216 A1 | 11/2002 | Liu et al. |
| 2003/0130187 A1 | 7/2003 | Reddy et al. |
| 2004/0132178 A1 | 7/2004 | Haines et al. |

FOREIGN PATENT DOCUMENTS

| | | |
|---|---|---|
| AU | 756554 | 4/1999 |
| WO | WO 99/08706 | 2/1999 |
| WO | WO 99/18214 | 4/1999 |
| WO | WO 99/29871 | 6/1999 |
| WO | WO 99/45956 | 6/1999 |
| WO | WO 99/53047 | 10/1999 |
| WO | WO 00/01409 | 1/2000 |
| WO | WO 00/26395 | 5/2000 |
| WO | WO 00/47756 | 8/2000 |
| WO | WO 00/77216 | 12/2000 |
| WO | WO 01/16330 | 3/2001 |
| WO | WO 01/83737 | 11/2001 |
| WO | WO 02/077210 | 10/2002 |

OTHER PUBLICATIONS

Certified English translation of PCT publication No. WO 00/47756, published Aug. 17, 2000, entitled "Recombined Porcine Adenovirus Based Viral Vaccines and Vectors," 60 pages.
Allan, G. M. and Ellis, J. A. (2000). "Porcine Circoviruses: A Review," *J. Vet. Diagn. Invest.* 12:3-14.
Allan, G. M. et al. (1994). "Some Biological and Physico-Chemical Properties of Porcine Circovirus," *M. Vet Med.* B. 41:17-26.
Allan, G. M. et al. (1995). "Pathogenesis of Porcine Circovirus; Experimental Infections of Colostrum Deprived Piglets and Examination of Pig Foetal Material," *Veterinary Microbiology* 44:49-64.
Allan, G. M. et al. (1998). "Isolation of Porcine Circovirus-Like Viruses from Pigs with a Wasting Disease in the USA and Europe," in this European *J. Vet. Diagn. Invest.* 10:3-10.
Chartier, C. et al. (Jul. 1996). "Efficient Generation of Recombinant Adenovirus Vectors by Homologous Recombination in *Escherichia coli*," *J. Virol.* 70(7):4805-4810.
Chroboczek, J. et al. (1992). "The Sequence of the Genome of Adenovirus Type 5 and Its Comparison with the Genome of Adenovirus Type 2," *Virology* 186:280-285.
Ellis J. et al. (1999). "Reproduction of Lesions of Postweaning Multisystemic Wasting Syndrome in Gnotobiotic Piglets," *J. Vet. Diagn. Invest.* 11:3-14.
Ellis, J. et al. (Jan. 1998). "Isolation of Circovirus from Lesions of Pigs with Postweaning Multisystemic Wasting Syndrome," *Can. Vet. J.* 39:44-51.
English translation of PCT publication No. WO 99/29871, entitled Circovirus Sequences Associated With Piglet Weight Loss Disease (PWD), 112 pages, 1999.
Flint, S. J. (1986). "Regulation of Adenovirus mRNA Formation," *Advances in Virus Research* 31:169-228.
Flint, S. J. et al. (1982). "Expression of Adenoviral Genetic Information in Productively Infected Cells," *Biochem. Biophys. Acta* 651:175-208.
Grand, R. J. A. (1987). "The Structure and Functions of the Adenovirus Early Region 1 Proteins," *Biochem. J.* 241:25-38.
Hamel, A. L. et al. (Jun. 1998). "Nucleotide Sequence of Porcine Circovirus Associated with Postweaning Multisystemic Wasting Syndrome in Pigs," *J. Virol.* 72(6):5262-5267.
Hamel, A. L. et al. (May 1998). Genbank Accession No. AF027217. Porcine Circoviru . . . [gi:2689645]. "Nucleotide Sequence of Porcine Circovirus Associated with Postweaning Multisystemic Wasting Syndrome in Pigs,", total pp. 4.
Hirt, B. (1967). "Selective Extraction of Polyma DNA from Infected Mouse Cell Cultures," *J. Mol. Biol.* 26:365-369.

(Continued)

*Primary Examiner*—Stacy B. Chen
(74) *Attorney, Agent, or Firm*—Morrison & Foerster LLP (57) ABSTRACT

The present invention relates to methods for culturing circovirus and in particular, porcine circovirus. The present invention provides compositions and methods for culturing porcine circovirus in mammalian cells expressing mammalian adenovirus E1 function.

10 Claims, 4 Drawing Sheets

OTHER PUBLICATIONS

Kennedy, S. et al. (2000). "Reproduction of Lesions of Postweaning Multisystemic Wasting Syndrome by Infection of Conventional Pics with Porcine Circovirus Type 2 Alone or in Combination with Porcine Parvovirus," *Journal of Comparative Pathology* 122(1):9-24.

Kleiboeker, S. B. (1995). "Identification and Sequence Analysis of the E1 Genomic Region of a Porcine Adenovirus," *Virus Res.* 36:259-268.

Krakowka, S, et al. (2000). "Viral Wasting Syndrome of Swine: Experimental Reproduction of Postweaning Multisystemic Wasting Syndrome in Gnotobiotic Swine by Coinfection with Porcine Circovirus 2 and Porcine Parvovirus," *Vet. Pathol.* 37:254-263.

Liu, Q et al. (2001). "Bacterial Expression of an Immunologically Reactive PCV2 ORF2 Fusion Protein," *Protein Express and Purif.* 21:115-120.

Liu, Q et al. (Sep. 2000). "Quantitative Competitive PCR Analysis of Porcine Circovirus DNA in Serum from Pigs with Postweaning Multisystemic Wasting Syndrome," *J. Clin. Microbiol.* 38(9):3474-3477.

Liu, Q. et al. (2001). "Nuclear Localization of the ORF2 Protein Encoded by Porcine Circovirus Type 2," *Virology* 285(1):91-99.

Lukert, P. D. et al. (1995). "Circoviridae", *In Virus Taxonomy: Classification and Nomenclature of Viruses.* F. A. Murphy, et al. (eds.) Sixth Report of the International Committee on Taxonomy of Viruses, Virology Division International Union of Microbiological Societies, Springer-Verlag Wien New York. pp. 166-168.

Mahé, D. et al. (2000). "Differential Recognition of ORF2 Protein from Type 1 and Type 2 Porcine Circoviruses and Identification of Immunorelevant Epitopes," *J. Gen. Virol.* 81:1815-1824.

Mankertz, A. et al. (1998). "Identification of a Protein Essential for Replication of Porcine Circovirus," *J. Gen. Virol.* 79:381-384.

Mankertz, A. et al. (2000). "Characterisation of PCV-2 Isolates from Spain, Germany, and France," *Virus Res.* 66:65-77.

Mankertz, A. et al. (Mar. 1997). "Mapping and Characterization of the Origin of DNA Replication of Porcine Circovirus," *J. Virol.* 71(3):2562-2566.

Meehan, B. M. et al. (1997). "Sequence of Porcine Circovirus DNA: Affinities with Plant Circoviruses," *J. Gen. Virol.* 78:221-227.

Meehan, B. M. et al. (1998). "Characterization of Novel Circovirus DNAs Associated with Wasting Syndromes in Pigs," *J. Gen. Virol.* 79:2171-2179.

Morozov, I. et al. (Sep. 1998). "Detection of a Novel Strain of Porcine Circovirus in Pigs with Postweaning Multisystemic Wasting Syndrome," *J. Clin. Microbiol.* 36(9):2535-2541.

Murphy, F. A. et al. eds. (1999). "Circoviridae" Chapter 22 *In Veterinary Virology*, 3rd ed. Academic Press, p. 357-361.

Nagy, M. et al. (2001). "The Complete Nucleotide Sequence of Porcine Adenovirus Serotype 5". *Journal of General Virology* 82(3):525-529.

Nagy, M. and Tuboly, T. (2000). "Porcine Adenoviruses: An Update On Genome Analysis and Vector Development," *Acta Veterinaria Hungarica* 48(4):491-499.

Nawagitgul, P. et al. (2000). "Open Reading Frame 2 of Porcine Circovirus Type 2 Encodes a Major Capsid Protein," *J. Gen. Virol.* 81:2281-2287.

Pogranichnyy, R. M. et al. (2000). "Characterization of Immune Response of Young Pigs to Porcine Circovirus Type 2 Infection," *Viral. Immunol.* 13(2):143-153.

Reddy, P. A. et al. (1999). "Replication-Defective Bovine Adenovirus Type 3 as an Expression Vector," *Journal of Virology* 73(11):9137-9144.

Reddy, P. S. et al. (Feb. 1998). "Nucleotide Sequence, Genome Organization, and Transcription Map of Bovine Adenovirus Type 3," *J. of Virol.* 72(2):1394-1402.

Reddy, P. S. et al. (1999). "Porcine Adenovirus-3 As A Helper-Dependent Expression Vector," *J. Gen. Virol.* 80:2909-2916.

Reddy, P. S. et al. (1995). "Comparison of the Inverted Terminal Repetition Sequences from Five Porcine Adenovirus Serotypes," Virology212(1):237-239.

Sambrook, J. et al., (1989) *Molecular Cloning: A Laboratory Manual*, 2nd Edition, Cold Spring Harbor Laboratory Press, p. 7.52 entitled "Hybridization and Autoradiography".

Shenk, T. (1996). "Chapter 30: Adenoviridae: The Viruses and Their Replications," *In Fields Virology*. 3rd ed. B.N. Fields, D.M. Knipe and P.M. Howley eds., Lippincott-Raven Publishers, Philadelphia, pp. 979-1016.

Shenk, T. (1996). "Adenoviridae: The Viruses and Their Replications," *In Fields Virology*. 3rd ed. B.N. Fields, D.M. Knipe and P.M. Howley eds., Lippincott-Raven Publishers, Philadelphia, pp. 2111-2148.

Tischer, I. et al. (1987). "Replication of Porcine Circovirus: Induction by Glucosamine and Cell Cycle Dependence," *Arch. Virol.* 96:39-57.

Tischer, I. D. et al. (1995). "Occurrence and Role of an Early Antigen and Evidence for Transforming Ability of Porcine Circovirus," *Arch. Virol.* 140:1799-1816.

Tischer, I. et al. (1986). "Studies on Epidemiology and Pathogenicity of Porcine Circovirus," *Arch. Virol.* 91:271-276.

Tischer, I. et al. (Jan. 1982). "A Very Small Porcine Virus with Circular Single-Stranded DNA," *Nature* 295:64-66.

Tuboly, T. et al. (1993). "Potential Viral Vectors for the Stimulation of Mucosal Antibody Responses Against Enteric Viral Antigens in Pigs," *Research in Veterinary Science* 54(3):345-350.

Tuboly, T. et al. (1995). "Restriction Endonuclease Analysis and Physical Mapping of the Genome of Porcine Adenovirus Type 5," *Virus Research* 37(1):49-54.

Tuboly, T. et al. (2000). "Characterization of Early Region 4 of Porcine Adenovirus Serotype 5," *Virus Genes* 20(3):217-219.

Tuboly, T. et al. (2000). "Sequence Analysis and Deletion of Porcine Adenovirus Serotype 5 E3 Region," Virus Research 68(2):109-117.

Tuboly, T. et al. (2001). "Construction and Characterization of Recombinant Porcine Adenovirus Serotype 5 Expressing the Transimissible Gastroenteritis Virus Spike Gene," *Journal of General Virology* 82(1):183-190.

Wang, L. et al. (Sep. 1998). Genbank Accession No. AF086834. Porcine Circoviru . . . [gi:3661515]. "Porcine Cirovirus Strain B9, Complete Genome," total pp. 4.

Wang, L. et al. (Sep. 1998). Genbank Accession No. AF086835. Porcine Circoviru . . . [gi:3661518]. "Porcine Circovirus Strain 9741, Complete Genome," total pp. 3.

Wang, L. et al. (Sep. 1998). Genbank Accession No. AF086836. Porcine Ciroviru . . . [gi:3661521]. "Porcine Circovirus Strain M226, Complete Genome," total pp. 3.

```
   1 accagcgcac ttcggcagcg gcagcacctc ggcaacacct cagcagcaac atgcccagca
  61 agaagaatgg aagaagcgga ccccaaccac ataaaaggtg ggtgttcacg ctgaataatc
 121 cttccgaaga cgagcgcaag aaaatacggg agctcccaat ctccctattt gattatttta
 181 ttgttggcga ggagggtaat gaggaaggac gaacacctca cctccagggg ttcgctaatt
 241 ttgtgaagaa gcaaactttt aataaagtga agtggtattt gggtgcccgc tgccacatcg
 301 agaaagccaa aggaactgat cagcagaata aagaatattg tagtaaagaa ggcaacttac
 361 ttattgaatg tggagctcct cgatctcaag gacaacggag tgacctgtct actgctgtga
 421 gtaccttgtt ggagagcggg attctggtga ccgttgcaaa gcagcaccct gtaacgtttg
 481 tcaaaaattt ccgcgggctg gctgaacttt tgaaagtgag cgggaaaatg caaaagcgtg
 541 attggaaaac caatgtacac ttcattgtgg ggccacctgg gtgtggtaaa agcaaatggg
 601 ctgctaattt tgcaaacccg gaaaccacat actggaaacc acctaaaaac aagtggtggg
 661 atggttacca tggtgaaaaa gtggttgtta ttgatgactt ttatggctgg ctgccgtggg
 721 atgatctact gagactgtgt gatcgatatc cattgactgt aaaaactaaa ggtggaactg
 781 tacctttttt ggcccgcagt attctgatta ccagcaatca aaccccgttg gaatggtact
 841 cctcaactgc tgtcccagct gtagaagctc tctatcggag gattacttcc ttggtattttt
 901 ggaagaatgt tacagaacaa tccacggagg aaggggggcca gtttgtcacc ctttccccccc
 961 catgccctga atttccatat gaaataaatt actgagtctt ttttatcact tcgtaatggt
1021 ttttattatt catttagggt ttaagtgggg ggtctttaag attaaattct ctgaattgta
1081 catacatggt tacacggata ttgtagtcct ggtcgtattt actgttttcg aacgcagtgc
1141 cgaggcctac gtggtccaca tttctagagg tttgtagcct cagccaaagc tgattccttt
1201 tgttatttgg ttggaagtaa tcaatagtgg agtcaagaac aggtttgggt gtgaagtaac
1261 gggagtggta ggagaagggt tggggattg tatggcggga ggagtagttt acatatgggt
1321 cataggttag ggctgtggcc tttgttacaa agttatcatc tagaataaca gcagtggagc
1381 ccactccccct atcaccctgg gtgatggggg agcagggcca gaattcaacc ttaaccttc
1441 ttattctgta gtattcaaag ggtatagaga ttttgttggt cccccctccc gggggaacaa
1501 agtcgtcaat attaaatctc atcatgtcca ccgcccagga gggcgttgtg actgtggtag
1561 ccttgacagt atatccgaag gtgcgggaga ggcgggtgtt gaagatgcca tttttccttc
1621 tccaacggta gcggtggcgg gggtggcacga gccagggggcg gcggcggagg atctggccaa
1681 gatggctgcg gggcggtgt cttcttctgc ggtaacgcct ccttggatac gtcatagctg
1741 aaaacgaaag aagtgcgctg taagtatt
```

FIG. 3A

MPSKKNGRSGPQPHKRWVFTLNNPSEDERKKIRELPISLFDYFI
VGEEGNEEGRTPHLQGFANFVKKQTFNKVKWYLGARCHIEKAKGTDQQNKEYCSKEGN
LLIECGAPRSQGQRSDLSTAVSTLLESGILVTVAKQHPVTFVKNFRGLAELLKVSGKM
QKRDWKTNVHFIVGPPGCGKSKWAANFANPETTYWKPPKNKWWDGYHGEKVVVIDDFY
GWLPWDDLLRLCDRYPLTVKTKGGTVPFLARSILITSNQTPLEWYSSTAVPAVEALYR
RITSLVFWKNVTEQSTEEGGQFVTLSPPCPEFPYEINY

FIG. 3B

MTYPRRRYRRRRHRPRSHLGQILRRRPWLVHPRHRYRWRRKNGI
FNTRLSRTFGYTVKATTVTTPSWAVDMMRFNIDDFVPPGGGTNKISIPFEYYRIRKVK
VEFWPCSPITQGDRGVGSTAVILDDNFVTKATALTYDPYVNYSSRHTIPQPFSYHSRY
FTPKPVLDSTIDYFQPNNKRNQLWLRLQTSRNVDHVGLGTAFENSKYDQDYNIRVTMY
VQFREFNLKDPPLKP

FIG. 3C

SEQUENCE LISTING

```
<160> NUMBER OF SEQ ID NOS: 3

<210> SEQ ID NO 1
<211> LENGTH: 1768
<212> TYPE: DNA
<213> ORGANISM: Porcine circovirus

<400> SEQUENCE: 1
accagcgcac ttcggcagcg gcagcacctc ggcaacacct cagcagcaac atgcccagca     60
agaagaatgg aagaagcgga ccccaaccac ataaaaggtg ggtgttcacg ctgaataatc    120
cttccgaaga cgagcgcaag aaaatacggg agctcccaat ctccctattt gattatttta    180
ttgttggcga ggagggtaat gaggaaggac gaacacctca cctccagggg ttcgctaatt    240
ttgtgaagaa gcaaactttt aataaagtga agtggtattt gggtgcccgc tgccacatcg    300
agaaagccaa aggaactgat cagcagaata aagaatattg tagtaaagaa ggcaacttac    360
ttattgaatg tggagctcct cgatctcaag gacaacggag tgacctgtct actgctgtga    420
gtaccttgtt ggagagcggg attctggtga ccgttgcaaa gcagcaccct gtaacgtttg    480
tcaaaaattt ccgcgggctg gctgaacttt tgaaagtgag cgggaaaatg caaaagcgtg    540
attggaaaac caatgtacac ttcattgtgg ggccacctgg gtgtggtaaa agcaaatggg    600
ctgctaattt tgcaaacccg gaaaccacat actggaaacc acctaaaaac aagtggtggg    660
atggttacca tggtgaaaaa gtggttgtta ttgatgactt ttatggctgg ctgccgtggg    720
atgatctact gagactgtgt gatcgatatc cattgactgt aaaaactaaa ggtggaactg    780
```

-continued

```
taccttttt   ggcccgcagt   attctgatta   ccagcaatca   aacccgttg    gaatggtact    840
cctcaactgc   tgtcccagct   gtagaagctc   tctatcggag   gattacttcc   ttggtatttt    900
ggaagaatgt   tacagaacaa   tccacggagg   aaggggggcca  gtttgtcacc   ctttccccc     960
catgccctga   atttccatat   gaaataaatt   actgagtctt   ttttatcact   tcgtaatggt   1020
ttttattatt   catttagggt   ttaagtgggg   ggtctttaag   attaaattct   ctgaattgta   1080
catacatggt   tacacggata   ttgtagtcct   ggtcgtattt   actgttttcg   aacgcagtgc   1140
cgaggcctac   gtggtccaca   tttctagagg   tttgtagcct   cagccaaagc   tgattccttt   1200
tgttatttgg   ttgaagtaa    tcaatagtgg   agtcaagaac   aggtttgggt   gtgaagtaac   1260
gggagtggta   ggagaagggt   tggggggattg  tatgcggga    ggagtagttt   acatatgggt   1320
cataggttag   ggctgtggcc   tttgttacaa   agttatcatc   tagaataaca   gcagtggagc   1380
ccactcccct   atcaccctgg   gtgatggggg   agcagggcca   gaattcaacc   ttaacctttc   1440
ttattctgta   gtattcaaag   ggtatagaga   ttttgttggt   ccccctccc    ggggaacaa    1500
agtcgtcaat   attaaatctc   atcatgtcca   ccgcccagga   gggcgttgtg   actgtggtag   1560
ccttgacagt   atatccgaag   gtgcgggaga   ggcgggtgtt   gaagatgcca   tttttccttc   1620
tccaacggta   gcggtggcgg   gggtggacga   gccaggggcg   gcggcggagg   atctggccaa   1680
gatggctgcg   ggggcggtgt   cttcttctgc   ggtaacgcct   ccttggatac   gtcatagctg   1740
aaaacgaaag   aagtgcgctg   taagtatt                                            1768
```

<210> SEQ ID NO 2
<211> LENGTH: 314
<212> TYPE: PRT
<213> ORGANISM: Porcine circovirus

<400> SEQUENCE: 2

```
Met Pro Ser Lys Lys Asn Gly Arg Ser Gly Pro Gln Pro His Lys Arg
 1               5                  10                  15

Trp Val Phe Thr Leu Asn Asn Pro Ser Glu Asp Glu Arg Lys Lys Ile
            20                  25                  30

Arg Glu Leu Pro Ile Ser Leu Phe Asp Tyr Phe Ile Val Gly Glu Glu
        35                  40                  45

Gly Asn Glu Glu Gly Arg Thr Pro His Leu Gln Gly Phe Ala Asn Phe
    50                  55                  60

Val Lys Lys Gln Thr Phe Asn Lys Val Lys Trp Tyr Leu Gly Ala Arg
65                  70                  75                  80

Cys His Ile Glu Lys Ala Lys Gly Thr Asp Gln Gln Asn Lys Glu Tyr
                85                  90                  95

Cys Ser Lys Glu Gly Asn Leu Leu Ile Glu Cys Gly Ala Pro Arg Ser
            100                 105                 110

Gln Gly Gln Arg Ser Asp Leu Ser Thr Ala Val Ser Thr Leu Leu Glu
        115                 120                 125

Ser Gly Ile Leu Val Thr Val Ala Lys Gln His Pro Val Thr Phe Val
    130                 135                 140

Lys Asn Phe Arg Gly Leu Ala Glu Leu Leu Lys Val Ser Gly Lys Met
145                 150                 155                 160

Gln Lys Arg Asp Trp Lys Thr Asn Val His Phe Ile Val Gly Pro Pro
                165                 170                 175

Gly Cys Gly Lys Ser Lys Trp Ala Ala Asn Phe Ala Asn Pro Glu Thr
            180                 185                 190
```

```
Thr Tyr Trp Lys Pro Pro Lys Asn Lys Trp Trp Asp Gly Tyr His Gly
        195                 200                 205

Glu Lys Val Val Ile Asp Asp Phe Tyr Gly Trp Leu Pro Trp Asp
    210                 215                 220

Asp Leu Leu Arg Leu Cys Asp Arg Tyr Pro Leu Thr Val Lys Thr Lys
225                 230                 235                 240

Gly Gly Thr Val Pro Phe Leu Ala Arg Ser Ile Leu Ile Thr Ser Asn
                245                 250                 255

Gln Thr Pro Leu Glu Trp Tyr Ser Ser Thr Ala Val Pro Ala Val Glu
            260                 265                 270

Ala Leu Tyr Arg Arg Ile Thr Ser Leu Val Phe Trp Lys Asn Val Thr
        275                 280                 285

Glu Gln Ser Thr Glu Glu Gly Gly Gln Phe Val Thr Leu Ser Pro Pro
    290                 295                 300

Cys Pro Glu Phe Pro Tyr Glu Ile Asn Tyr
305                 310

<210> SEQ ID NO 3
<211> LENGTH: 233
<212> TYPE: PRT
<213> ORGANISM: Porcine circovirus

<400> SEQUENCE: 3

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```

METHODS TO CULTURE CIRCOVIRUS

CROSS-REFERENCE TO RELATED APPLICATIONS

This application is a divisional application of U.S. patent application Ser. No. 10/112,540, filed Mar. 27, 2002, now U.S. Pat. No. 6,794,163, which claims the benefit of U.S. Provisional Application Ser. No. 60/279,173, filed Mar. 27, 2001, all of which are hereby incorporated by reference herein in their entirety.

TECHNICAL FIELD

The present invention relates to the field of circovirus and provides compositions and methods for culturing circovirus, in particular porcine circovirus. In particular, the present invention relates to methods for culturing porcine circovirus in mammalian cells expressing a mammalian adenovirus E1 gene function.

BACKGROUND ART

A family of viruses, named Circoviridae, found in a range of plant and animal species and commonly referred to as circoviruses, are characterized as round, non-enveloped virions with mean diameters from 17 to 23.5 nm containing circular, single-stranded deoxyribonucleic acid (ssDNA). The ssDNA genome of the circoviruses represent the smallest viral DNA replicons known. As disclosed in WO 99/45956, at least six viruses have been identified as members of the family according to The Sixth Report of the International Committee for the Taxonomy of Viruses (Lukert, P. D. et al. 1995, *The Circoviridae*, pp. 166–168. In F. A. Murphy, et al. (eds.) Virus Taxonomy, Sixth Report of the International Committee on Taxonomy of Viruses, Arch. Virol. 10 Suppl.).

Animal viruses included in the family are chicken anemia virus (CAV); beak and feather disease virus (BFDV); porcine circovirus (PCV); and pigeon circovirus. PCV was originally isolated in porcine kidney cell cultures. PCV replicates in the cell nucleus and produces large intranuclear inclusion bodies. See Murphy et al. (1999, *Circoviridae p.* 357–361, Veterinary Virology, 3rd ed. Academic Press, San Diego). There are currently two recognized types of PCV, PCV type 1 (PCV1) and PCV type 2 (PCV2). PCV1, isolated as a persistent contaminant of the continuous porcine kidney cell line PK-15 (ATCC CCL31), does not cause detectable cytopathic effects in cell culture and fails to produce clinical disease in pigs after experimental infection (see Allan G., 1995, *Vet. Microbiol.* 44: 49–64; Tischer, I. et al., 1982, *Nature* 295:64–66; and Tischer, I. et al., 1986, *Arch. Virol.* 91:271–276). PCV2, in contrast to PCV1, is closely associated with post weaning multisystemic wasting syndrome (PMWS) in weanling pigs (see Allan G. et al., 1998, *Europe. J. Vet. Diagn. Investig.* 10:3–10; Ellis, J. et al., 1998, *Can. Vet. J.* 39:44–51 and Morozov, I. et al., 1998, *J. Clin. Microbiol.* 36:2535–2541). The nucleotide sequences for PCV1 are disclosed in Mankertz, A., et al. (1997, *J. Virol.* 71:2562–2566) and Meehan, B. M., et al. (1997, *J. Gen. Virol.* 78:221–227) and the nucleotide sequences for PCV2 are disclosed in Hamel, A. L. et al. (1998, *J. Virol.* 72:5262–5267); Mankertz, A. et al. (2000, *Virus Res.* 66:65–77) and Meehan, B. M. et al. (1998, *J. Gen. Virol.* 79:2171–2179). Strains of PCV2 are disclosed in WO 00/01409 and have been deposited at the European Collection of Cell Cultures, Centre for Applied Microbiology & Research, Porton Down, Salisbury, Wiltshire SP4 OJG, United Kingdom and include: accession No. V97100219; accession No. V9700218; accession No. V97100217; accession No. V98011608; and accession No. V98011609. WO 00/77216 also discloses PCV2.

Published studies to date on PCV2 used either tissue homogenate or cultured virus derived from field isolates. Tischer et al. (1987, *Arch Virol.* 96:39–57) report that porcine kidney cells are stimulated to entry to the S phase in the cell cycle by D-glucosamine treatment. However, the treatment must be performed with caution because D-glucosamine is toxic for cell culture (see, Allan et al., (2000). *J. Vet. Diagn. Investigation.* 12:3–14). There remains a need for methods for culturing circovirus, such as for example, PCV1 and PCV2, and other circoviruses, such that pure circovirus is obtained. Such methods would be advantageous, in particular for preparation of PCV2 antigens as vaccines directed against PMWS. The present invention addresses that need.

All patents and publications are hereby incorporated herein in their entirety.

DISCLOSURE OF THE INVENTION

The present invention provides methods for culturing mammalian circovirus comprising: a) obtaining mammalian cells expressing a mammalian adenovirus E1 function, wherein said cells are permissive for mammalian circovirus replication; b) introducing said mammalian circovirus genome, or a portion thereof capable of replication, into said mammalian cells; and c) culturing said mammalian cells under conditions suitable for replication of said mammalian circovirus. In some embodiments, the method further comprises recovering said circovirus from said cultured cells.

In some embodiments, the mammalian circovirus is porcine circovirus, such as for example, porcine circovirus 1 (PCV1) or porcine circovirus 2 (PCV2). In yet additional embodiments, the porcine circovirus comprises a chimeric nucleotide sequence. In other embodiments, the mammalian cells are of porcine origin. In yet other embodiments, the mammalian cells are porcine retina cells.

In other embodiments, the mammalian adenovirus E1 function is human adenovirus E1 function. In yet other embodiments, the mammalian adenovirus E1 function is porcine adenovirus E1 function. In further embodiments, the E1 function is E1A and/or E1B function. In yet further embodiments, the mammalian cell expressing the mammalian E1 function is stably transformed with mammalian E1 gene sequences. In other embodiments, the mammalian E1 gene sequence is heterologous to said mammalian cell.

The present invention also provides recombinant mammalian cells that express a mammalian adenovirus E1 function and comprise a mammalian circovirus genome, or a portion thereof capable of replication, and wherein said cells are permissive for the replication of said mammalian circovirus. In some embodiments, the mammalian circovirus is porcine circovirus, such as for example, porcine circovirus 1 (PCV1) or porcine circovirus 2 (PCV2). In yet additional embodiments, the porcine circovirus comprises a chimeric nucleotide sequence. In some embodiments, the adenovirus E1 function is human adenovirus E1 function. In other embodiments, the E1 function is porcine adenovirus E1 function. In other embodiments, the mammalian cell is of porcine origin. In further embodiments, the mammalian cell is a porcine retinal cell. In yet further embodiments, the mammalian cell expressing the mammalian E1 function is stably transformed with mammalian adenovirus E1 gene sequences. In other embodiments, the mammalian E1 gene sequence is heterologous to said mammalian cell.

The present invention also provides methods of preparing a recombinant mammalian cell expressing a mammalian adenovirus E1 function and comprising a mammalian circovirus genome comprising the steps of, a) obtaining a mammalian cell expressing a mammalian adenovirus E1 function; and b) introducing said mammalian circovirus genome, or a portion thereof capable of replication, into said mammalian cell. In additional embodiments, the method comprises the additional step of culturing the recombinant mammalian cell under conditions suitable for the replication of said mammalian circovirus. In further embodiments, the method comprises recovering said circovirus from said cultured cells. In some embodiments, the mammalian circovirus is porcine circovirus, such as for example, porcine circovirus 1 (PCV1) or porcine circovirus 2 (PCV2). In yet additional embodiments, the porcine circovirus comprises a chimeric nucleotide sequence. In further embodiments, the mammalian cells are of porcine origin. In yet further embodiments, the mammalian cells are porcine retina cells. In additional embodiments, the adenovirus E1 function is human adenovirus E1 function or porcine adenovirus E1 function. In yet further embodiments, the mammalian cell expressing the mammalian adenovirus E1 function is stably transformed with mammalian adenovirus E1 gene sequences. In other embodiments, the mammalian E1 gene sequence is heterologous to said mammalian cell.

BEST MODE FOR CARRYING OUT THE INVENTION

Figures 1A, 1B:
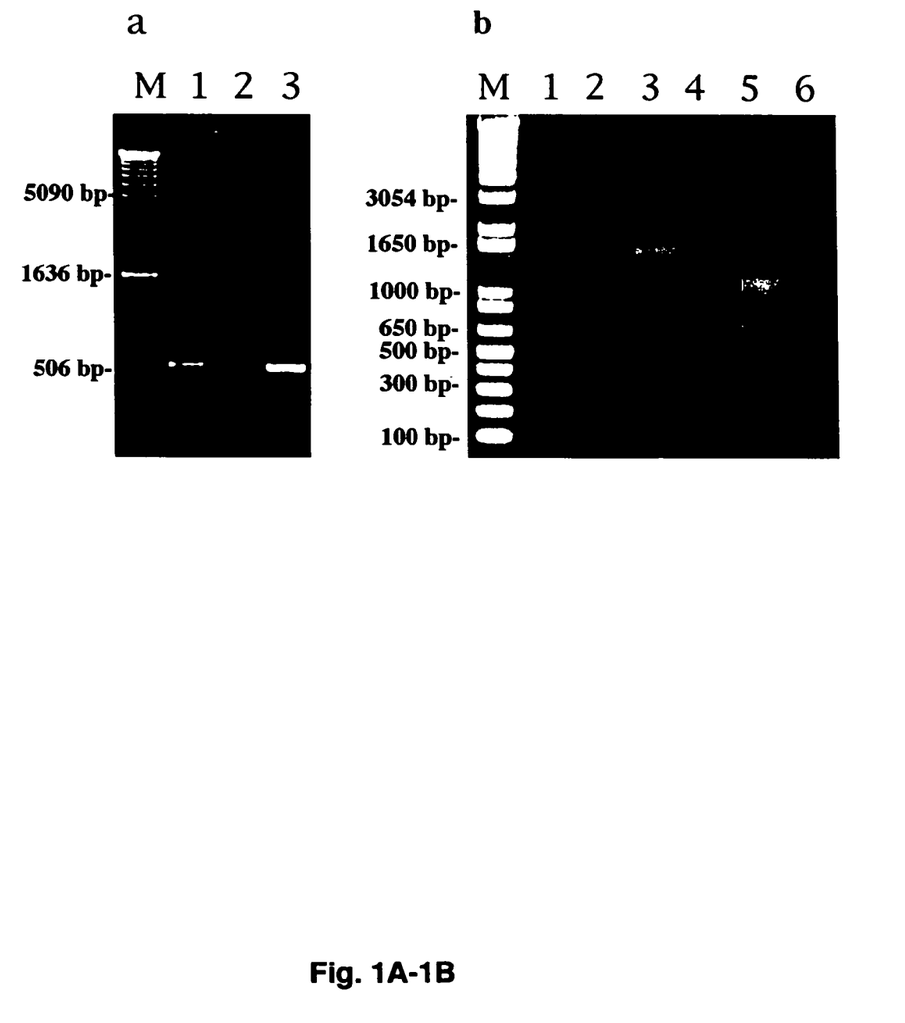
FIGS. 1A–1B provide the characterization and titration of PCV2 virus generated by DNA transfection and extraction from infected VIDO R1 cells by Hirt's method. (A) PCR using PCV2-specific primers and DNA from PCV2-infected (lane 1) and mock-infected (lane 2) cells. A plasmid containing PCV2 genome was used as a control (lane 3). The 1-kb DNA ladder from GIBCO BRL was loaded in lane M. (B) Viral DNA from PCV2-infected (lanes 1, 3, and 5) and mock-infected (lanes 2, 4, and 6) cells were digested with NcoI and StuI (lanes 1 and 2), EcoRI and StuI (lanes 3 and 4), and EcoRI and EcoRV (lanes 5 and 6). The 1-kb-plus DNA ladder from GIBCO BRL was loaded in lane M.
Figures 2A, 2B:
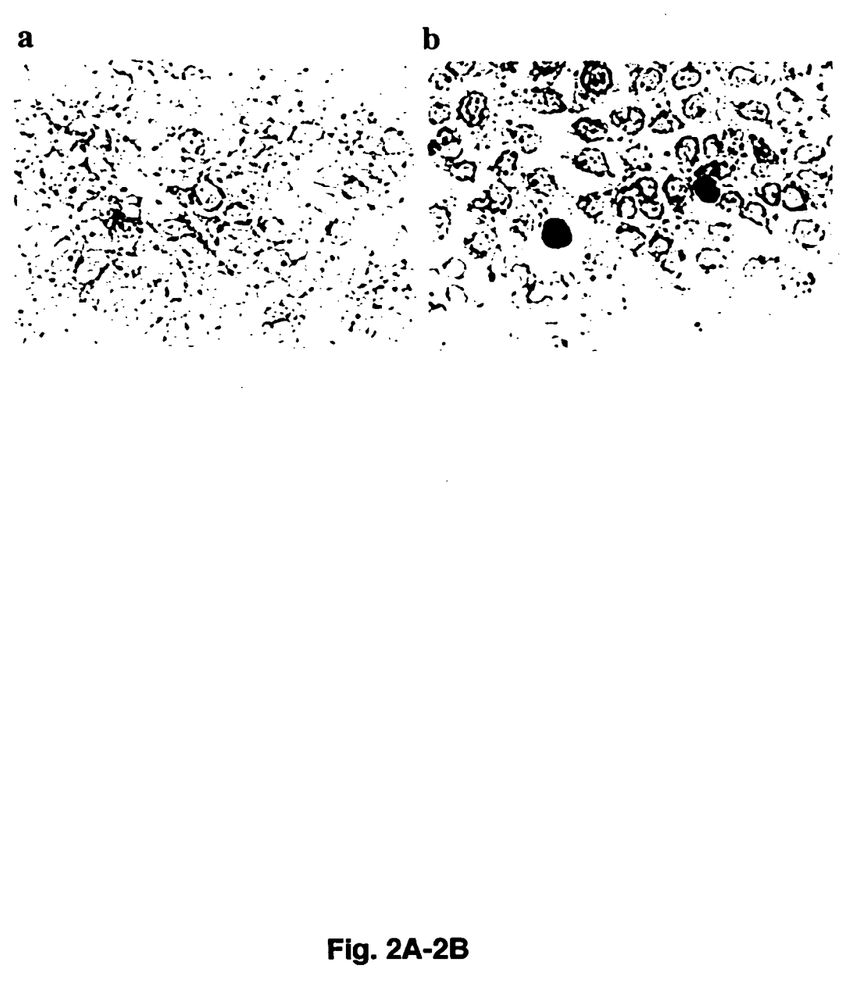
FIGS. 2A–2B depict titration of PCV2 by immunoperoxidase staining. At 72 h.p.i., mock- (A) or PCV2- (B) infected VIDO R1 cells were incubated with rabbit anti-ORF2 polyclonal antibody and biotinylated secondary antibody. After application of an avidin and biotinylated horseradish peroxidase complex, the monolayer was developed by diaminobenzidine tetrahydrochloride (DAB). One dark cell resulted from one virus particle infection.
Figure 3A:
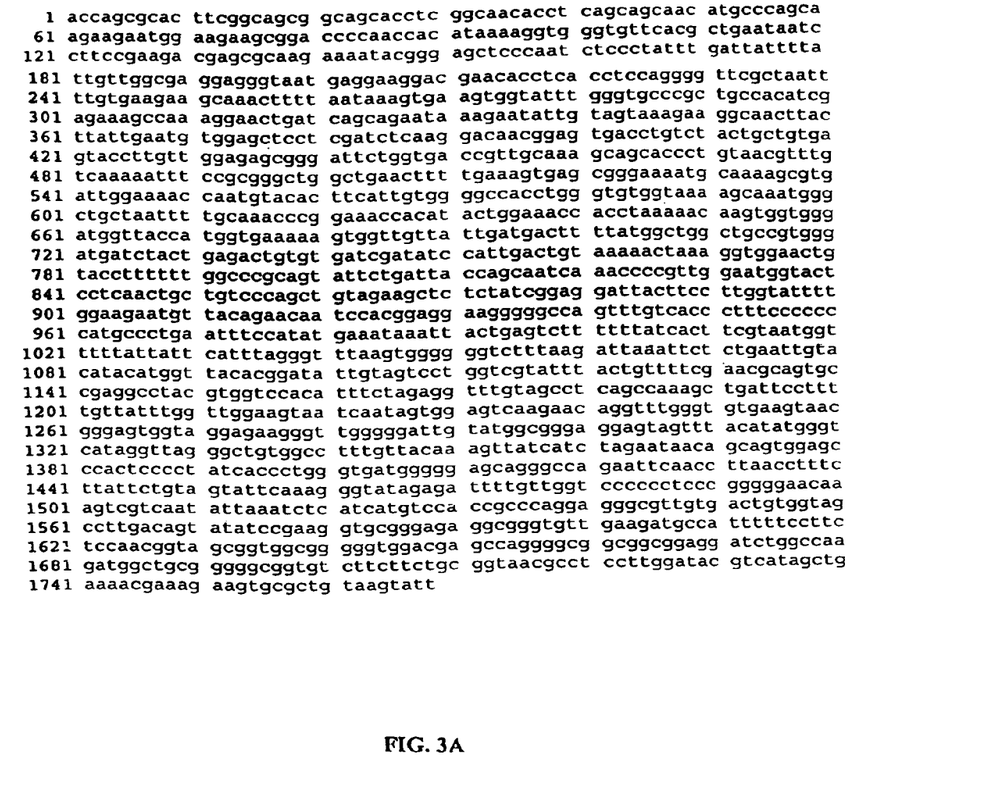
FIGS. 3A–3C show the nucleotide sequence (A) (SEQ IID NO:1) and amino acid sequence for ORF 1 (B) (SEQ ID NO:2) and ORF 2 (C) (SEQ ID NO:3) of porcine circovirus 2 (PCV2) as described in Genbank accession number AF086834.
Figure 3B:
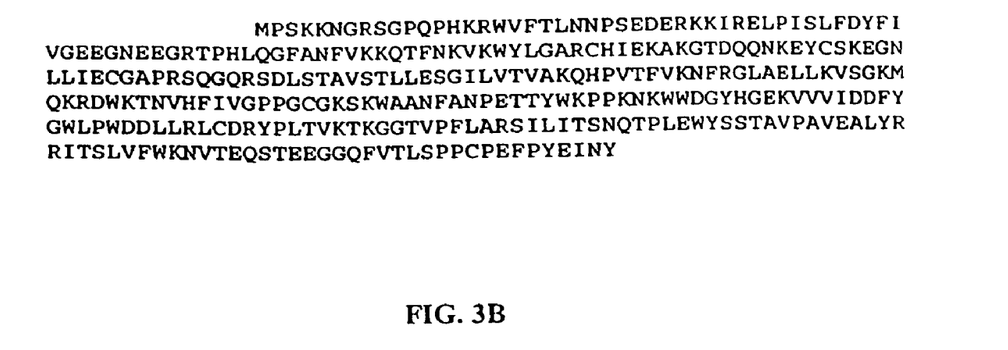
Figure 3C:
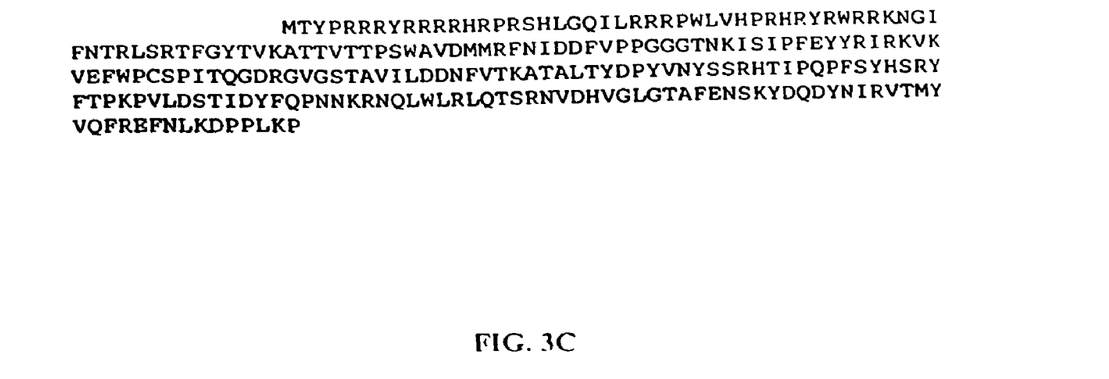

The present invention relates to compositions and methods for culturing mammalian circovirus, in particular porcine circovirus. The present invention is based on the finding that a porcine cell expressing human E1 function was able to be transfected with a PCV2 virus genome and generated PCV2 virus with a high virus titer. VIDO R1 cell line, deposited with the ATCC and having ATCC accession number PTA-155, is a porcine retina cell line transformed with human adenovirus-5 (HAV5) E1, that has been shown to induce the S phase of the cell cycle and transactivate transcription. See, Shenk, T. (1996). "*Adenoviridae*: the viruses and their replication" In *Fields Virology*. 3rd ed. B. N. Fields, D. M. Knipe and P. M. Howley (ed.)Lippincott-Raven Publishers, Philadelphia, New York, pp. 2111–2148. As described herein in Example 3, VIDO R1 cells, were transfected with a PCV2 genome and generated virus at $2\times10^7$ IU/ml.

The practice of the present invention employs, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984); Ausubel, et al., *Current Protocols In Molecular Biology*, John Wiley & Sons (1987, 1988, 1989, 1990, 1991, 1992, 1993, 1994, 1995, 1996); and Sambrook et al., *Molecular Cloning: A Laboratory Manual* (2nd Edition); vols. I, II & III (1989).

Circoviridae, a family of viruses having round, non-enveloped virions with mean diameters from 17 to 23.5 nm containing circular, single-stranded DNA (ssDNA), are described in The Sixth Report of the International Committee for the Taxonomy of Viruses, supra. Members of the group include the porcine circoviruses, PCV1 and PCV2. Some of the PCVs are known to be pathogenic, such as PCV2, associated with PMWS.

Nucleotide sequences for PCV1 are provided in Mankertz, A., et al., 1997, *J. Virol.* 71:2562–2566 and Meehan, B. M. et al., 1997, *J. Gen. Virol.* 78:221–227. Nucleotide sequences for PCV2 are provided in Hamel, A. L. et al., 1998, *J. Virol.* 72:5262–5267; Mankertz, A. et al., 2000, *Virus Res.* 66:65–77 and Meehan, B. M. et al., 1998, *J. Gen. Virol.* 79:2171–2179. Representative strains of PCV2 have been deposited with the European Collection of Cell Cultures, Centre for Applied Microbiology & Research, Porton Down, Salisbury, Wiltshire SP4 OJG, United Kingdom and include accession No. V97100219; accession No. V9700218; accession No. V97100217; accession No. V98011608; and accession No. V98011609. WO 00/77216 also discloses PCV2. PCV2 nucleotide sequences have also been published in Hamel et al., (1998), *J. Virol.* vol. 72, 6:5262-5267 (GenBank AF027217) and in Morozov et al., (1998), *J. Clinical Microb.* vol. 36, 9:2535–2541, as well as GenBank AF086834; AF086835; and AF086836. Comparison of the published nucleotide sequences for PCV1 and PCV2 reveals a <80% identity, although the genomic organization is similar, especially in the arrangement of the two largest open reading frames (ORFs) with a putative origin of DNA replication.

The present invention encompasses methods of culturing mammalian circovirus and in particular, porcine circovirus (PCV). The present invention encompasses methods of culturing PCV comprising the PCV nucleotide sequences disclosed herein or known in the art, or ORFs thereof, or portions thereof that are capable of replication. The present invention also encompasses methods of culturing PCV having PCV nucleotide sequences differing through the degeneracy of the genetic code to those disclosed herein or known in the art, or ORFs thereof, or portions thereof capable of replication. The present invention further encompasses methods of culturing PCV comprising PCV nucleotide sequence variations which do not change the functionality or strain specificity of the nucleotide sequence, or ORFs thereof, or portions thereof capable of replication. The present invention also encompasses methods of culturing PCV comprising PCV nucleotide sequences capable of hybridizing to those sequences disclosed herein under conditions of intermediate to high stringency, and methods of culturing PCV comprising mutations of the PCV nucleotide sequence disclosed herein or known in the art, such as deletions or point mutations, or ORFs thereof, or portions thereof, capable of replication. The present invention also encompasses methods of culturing PCV comprising heterologous nucleotide sequences. The present invention encompasses methods of culturing PCV that comprise chimeric circovirus nucleotide sequences, such as, for example, nucleotide sequences from porcine circovirus in fusion with nucleotide sequences from other pathogenic viruses, such as a pathogenic porcine virus, including parvovirus.

As used herein, a heterologous nucleotide sequence, with respect to a circovirus or mammalian cell, is one which is not normally associated with the circovirus sequences as part of the circovirus genome or one which is not normally associated with the mammalian cell, respectively. Heterologous nucleotide sequences include synthetic sequences. Hybridization reactions can be performed under conditions of different "stringency". Conditions that increase stringency of a hybridization reaction are widely known and published in the art. See, for example, Sambrook et al. (1989) at page 7.52. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. An exemplary set of stringent hybridization conditions is 68° C. and 0.1×SSC.

The PCV genomes encode several polypeptide sequences, ranging in approximate size from 8 to 35 kD. It is deemed routine to determine open reading frames (ORFs) for porcine circoviruses using standard software such as for example, MacVector® (Oxford Molecular Group Inc., MD 21030). The largest ORF, ORF1, of the two types of PCV shows only minor variation with an identity of 85% (as measured by the clustal program) and has been demonstrated to be the Rep protein in PCV1 (Mankertz, A., et al., 1998, *J. Gen. Virol.* 79:381–384). Without wanting to be bound by theory, a higher rate of variation displayed in the ORF2 sequences of PCV1 and PCV2 (identity about 65%) would suggest that type-specific features of PCV might be determined by the respective ORF2 protein. Several PCV type-specific epitopes have been mapped on PCV2 ORF2 sequences. See Mahe, D. et al., 2000, *J. Gen. Virol.* 81:1815–24. In another recent study, PCV2 ORF2 has been identified as a major structural protein that can form viral capsid-like particles in insect cells infected with ORF2 expressing recombinant baculovirus. See Nawagitgul, P. et al., 2000, *J. Gen. Virol.* 81:2281–2287.

In some illustrative embodiments of the invention disclosed herein, a recombinant vector comprising a PCV genome or an ORF thereof, or a portion thereof, such as an antigenic region, is constructed by in vitro recombination between a plasmid and a PCV genome. In some embodiments, the PCV genome is a PCV2 genome. In other embodiments, a recombinant vector comprising a PCV genome or an ORF thereof, or a portion thereof, such as an antigenic region, is constructed by in vivo recombination. Methods for in vivo recombination are know in the art and include, for example, the methods disclosed in Chartier, et al. (1996, *J. Virol.* 70:4805–4810). Vectors for constructing circovirus genomes include for example, bacterial plasmids which allow multiple copies of the cloned circovirus nucleotide sequence to be produced. In some embodiments, the plasmid is co-transfected into a suitable host cell for recombination. Suitable host cells for recombination include any cell that will support recombination between a PCV genome and a plasmid containing PCV sequences, or between two or more plasmids, each containing PCV sequences. Recombination is generally performed in procaryotic cells, such as *E. coli* for example, while generation of circovirus is preferably performed in mammalian cells permissive for PCV replication, such as for example porcine cells and in particular, porcine cells capable of expressing mammalian adenovirus E1 function.

The present invention encompasses the use of any mammalian host cell permissive for circovirus replication, and in particular, permissive for replication of PCV, such as PCV1 and PCV2. Allan et al. (1995, *Veterinary Microbiology* 44: 49–64) report that PCV replicate in porcine and bovine monocyte/macrophage cultures. Tischer et al. (1987, *Arch. Virol.* 96:39–57) report that PCV is known to require actively dividing cells for replication in cell culture. Examples of cells or cell lines useful for replication of PCV include mammalian cells comprising E1 function and permissive for PCV replication, including porcine cells, such as porcine monocyte/macrophage cells and porcine retinal cells, expressing adenovirus E1 function. In an illustrative embodiment disclosed herein, porcine retina cells expressing human adenovirus E1 function are shown to be permissive for replication of PCV2 and shown to generate virus at $2\times10^7$ IU/ml. Porcine cell lines are available from public sources such as for example, the American Type Tissue Collection (ATCC). The growth of bacterial cell cultures, as well as culture and maintenance of eukaryotic cells and mammalian cell lines are procedures well-known to those of skill in the art.

The present invention encompasses methods of culturing mammalian circovirus, in particular, porcine circovirus, in mammalian host cells transfected with mammalian adenovirus E1 gene sequences. In some embodiments, the mammalian cell is stably transformed with adenovirus E1 gene sequences. In some embodiments, the E1 gene sequences are integrated into the genome of the mammalian cell. In other embodiments, the E1 gene sequences are present on a replicating plasmid. In yet other embodiments, the E1 gene sequence is heterologous to the mammalian cell. In an illustrative embodiment disclosed herein a porcine mammalian cell is transformed with a human adenovirus 5 E1 gene sequence. The present invention encompasses the use of any mammalian cell or mammalian cell line expressing E1 function as long as the mammalian cell or cell line expressing E1 function is permissive for the replication of circovirus, in particular porcine circovirus, such as for example, porcine circovirus 1 or porcine circovirus 2. In preferred embodiments, the mammalian cell is a porcine cell or cell line. The present invention encompasses the use of any mammalian E1 function as long as the mammalian host cell expressing the mammalian E1 function is permissive for replication of circovirus, in particular, PCV, such as for example, porcine circovirus 1 or porcine circovirus 2. Mammalian adenovirus genomes are known in the art and are disclosed in, for example, Reddy et al. (1998, *Journal of Virology*, 72:1394) which discloses nucleotide sequence, genome organization, and transcription map of bovine adenovirus 3 (BAV3); and Kleiboeker (1995, *Virus Res.* 36:259–268), which discloses the E1 region of PAV-4. The present invention encompasses E1 function from any of the various serotypes of human adenovirus, such as Ad2, Ad5, Ad12, and Ad40. In an illustrative embodiment disclosed herein in Example 1, E1 function is human Ad5 E1 function. The human E1A gene is expressed immediately after viral infection (0–2 hours) and before any other viral genes. Flint (1982) *Biochem. Biophys. Acta* 651:175–208; Flint (1986) *Advances Virus Research* 31:169–228; Grand (1987) *Biochem. J.* 241:25-38. The transcription start site of Ad5 E1A is at nucleotide 498 and the ATG start site of the E1A protein is at nucleotide 560 in the virus genome. The E1B protein functions in trans and is necessary for transport of late mRNA from the nucleus to the cytoplasm. The E1B promoter of Ad5 consists of a single high-affinity recognition site for Spl and a TATA box. In particular, human adenovirus 5 E1A and E1B gene sequences are located at nucleotides 505–4034 of the nucleotide sequence provided in Chroboezek, J. et al. (1992, *Virology.* 186:280–285). In an illustrative embodiment disclosed herein in the Examples, the mammalian host cell is a porcine host cell transfected with human adenovirus 5 E1 gene sequences.

The PCV genome can be isolated from PCV virions, or can comprise a PCV genome that has been inserted into a plasmid, using standard techniques of molecular biology and biotechnology. Cloning of the full-length PCV2 genome into vector pBluescript II KS(+) from Strategene by PCR is described in Liu, et al. (2000, *J. Clin. Microbiol.* vol 38:3474–3477). The full-length PCV2 genome DNA can be released from the resulting plasmid upon SacII digestion.

Introduction of circovirus nucleotide sequences into permissive mammalian host cells can be achieved by any method known in the art, including, but not limited to, transfection and transformation including, but not limited to, microinjection, electroporation, $CaPO_4$ precipitation, DEAE-dextran, liposomes, particle bombardment, etc. An illustrative method for transfecting PCV2 nucleotide sequences into VIDO R1 cells is described herein in Example 3.

Methods for culturing procaryotic cells, such as bacterial cells, and eukaryotic cells, such as mammalian host cells expressing adenovirus E1 function are deemed routine to those of skill in the art.

The following examples are provided to illustrate but not limit the invention. All references and patent publications disclosed herein are hereby incorporated in their entirety by reference.

EXAMPLES

Example 1

Preparation of Porcine Retinal Cells Transfected with Human Adenovirus E1 Gene Sequences (VIDO R1 Cells)

Primary cultures of porcine embryonic retina cells were transfected with 10 µg of plasmid pTG 4671 (Transgene, Strasbourg, France) by the calcium phosphate technique. The pTG 4671 plasmid contains the entire E1A and E1B sequences (nts 505–4034) of HAV-5, along with the puromycin acetyltransferase gene as a selectable marker. In this plasmid, the E1 region is under the control of the constitutive promoter from the mouse phosphoglycerate kinase gene, and the puromycin acetyltransferase gene is controlled by the constitutive SV40 early promoter. Transformed cells were selected by three passages in medium containing 7 µg/ml puromycin, identified based on change in their morphology from single foci (i.e., loss of contact inhibition), and subjected to single cell cloning. The established cell line was first tested for its ability to support the growth of E1 deletion mutants of HAV-5. Subsequently the cell line was further investigated for the presence of E1 sequences in the genome by PCR, expression of the E1A and E1B proteins by Western blot, and doubling time under cell culture conditions. E1 sequences were detected, and production of E1A and E1B proteins was demonstrated by immunoprecipitation. Doubling time was shorter, when compared to that of the parent cell line.

To assess the stability of E1 expression, VIDO R1 cells were cultured through more than 50 passages (split 1:3 twice weekly) and tested for their ability to support the replication of E1-deleted HAV-5. Expression of the E1A and E1B proteins at regular intervals was also monitored by Western blot. The results indicated that the VIDO R1 line retained the ability to support the growth of E1-deleted virus and expressed similar levels of E1 proteins during more than 50 passages in culture. Therefore, VIDO R1 can be considered to be an established cell line. VIDO R1 cell line has been deposited with the American Type Culture collection (ATCC) and has ATCC accession number PTA-155.

Example 2

Example 2 provides a description of the molecular cloning of full-length PCV2 genome.

Initially, PCV2 DNA was amplified by PCR from total DNA extracted from a piglet with PMWS. The cloning of the full-length PCV2 genome DNA into vector pBluescript II KS(+) (Stratagene) by polymerase chain reaction (PCR) was described in Liu et al. (2000). *J. Clin. Microbiol.* 38:3474–3477). The PCV2 sequence was submitted to GenBank (Accession no. AF086834). The full-length PCV2 genome DNA is released from the resulting plasmid upon SacH digestion.

Example 3

Example 3 describes the transfection of VIDO R1 cells, as described in Example 1, with a plasmid containing the PCV2 genome as constructed in Example 2.

Material and Methods

Cell Culture

Fetal porcine retina cell line, VIDO R1, as described in Example 1 and Vero cells (ATCC) were maintained at 37° C. with 5% $CO_2$ in Eagles based MEM media supplemented with 10% or 5% heat-inactivated fetal bovine serum (FBS), respectively.

Transfection and Infection

Monolayers of VIDO R1 cells grown in a six-well dish were transfected with cloned PCV2 DNA using Lipofectin according to the manufacturer's recommendations (GIBCO BRL). Prior to transfection, PCV2 full-length genome was released from the plasmid by digestion with SacII (Liu, Q., et al., 2000, *J. Clin. Microbiol.* 38:3474–3477). For infection, the transfected VIDO R1 cells were subjected to three cycles of freezing (−70° C.) and thawing (37° C.). The lysate was then clarified by centrifugation and used to infect fresh VIDO R1 cells. In published reports, a PCV1-free porcine kidney cell line is used to culture PCV2 virus. To stimulate the entry to the S phase in the cell cycle, the porcine kidney cells are always treated by D-glucosamine (see Tischer et al., (1987). *Arch Virol.* 96:39–57.). However, the treatment must be performed with caution because D-glucosamine is toxic for cell culture (see, Allan et al., (2000). *J. Vet. Diagn. Investigation.* 12:3–14). In contrast, since the VIDO R1 cell line used in this study has been transformed by HAV5-E1 that can induce the S phase, the D-glucosamine treatment was not necessary.

Example 4

Virus Purification and Titration

For the purification of PCV2 virus, PCV2-infected VIDO R1 cells were incubated with 0.5% Triton X-114 in phosphate-buffered saline (PBS) at 37° C. for 45 min followed by Freon 113 (1,1,2-trichloro-trifluoroethane) extraction. The cell debris and membranes were clarified by centrifugation at 2000 g for 15 min. The viruses in the supernatant were pelleted at 35000 g for 3 h through a 20% sucrose cushion. The virus pellet was suspended in PBS and stored at −70° C. Virus titers were determined as infectious units (IU) by quantitative 0RF2 protein immuno-peroxidase staining. For this purpose, the cell monolayers in 12-well dishes were infected with serial dilutions of virus. After adsorption of virus for 1 h, the cells were washed and overlaid with MEM containing 2% FBS and 0.7% agarose. On day 3 post infection (p.i.), the agarose overlay was removed and the cells were fixed and permeabilized with methanol/acetone (1:1 in volume) for 20 min at −20° C. After blocking with 1% bovine serum albumin for 1 h at room temperature, the cells were incubated with rabbit anti-ORF2 serum (Liu et al., 2001, Protein Expression and Purification. 21:115–120). After 2 h incubation, the plates were washed with PBS and then processed using VECTASTAIN Elite ABC kit (Vector Laboratories). The reaction was developed with 3,3'diaminobenzidine (DAB) tetrahydrochloride and observed under a microscope. By counting the positively stained cells, the virus titer was expressed as IU where 1 IU was defined as one positively stained cell/foci at 3 d.p.i.

Viral DNA Extraction and Characterization

Viral DNA was extracted from PCV2-infected VIDO R1 cell monolayers by the method of Hirt (1967, *J. Mol. Biol.* 26:365–369). The viral DNA was then characterized by restriction analysis and polymerase chain reaction (PCR) as described in Liu et al., (2000). *J. Clin. Microbiol.* 38:3474–3477).

PCR using DNA extracted from the infected cells as template and PCV-2-specific primers amplified a product of specific size, while no DNA was amplified from control, uninfected cells. Consistent with the expected restriction patterns, digestions of viral DNA with NcoI and StuI resulted in two fragments of 1291 bp and 477 bp in size, respectively; digestion with EcoRI and StuI produced two fragments of 1492 bp and 276 bp in size, respectively; and digestion with EcoRI and EcoRV generated two fragments of 1094 bp and 674 bp in size, respectively. The data indicate that PCV2 virus was obtained. Using an immunostaining assay and by counting the positive stained cells, the virus titer of this preparation was determined to be $2\times10^7$ IU/ml.

We claim:

1. A recombinant mammalian cell that expresses a mammalian adenovirus E1 functional protein and comprises a porcine circovirus genome, or a portion thereof capable of replication, and wherein said cell is permissive for the replication of said porcine circovirus.

2. The recombinant mammalian cell of claim 1 wherein said adenovirus E1 functional protein is human adenovirus E1 functional protein.

3. The recombinant mammalian cell of claim 1 wherein said adenovirus E1 functional protein is porcine adenovirus E1 functional protein.

4. The recombinant mammalian cell of claim 1 wherein the mammalian cell expressing mammalian adenovirus E1 functional protein is stably transformed with a mammalian adenovirus E1 gene sequence.

5. The recombinant mammalian cell of claim 4 wherein said E1 gene sequence is a human adenovirus E1 gene sequence.

6. The recombinant mammalian cell of claim 4 wherein said mammalian adenovirus E1 gene sequence is heterologous to said mammalian cell.

7. The recombinant cell of claim 1 wherein said porcine circovirus is porcine circovirus 1.

8. The recombinant cell of claim 1 wherein said porcine circovirus is porcine circovirus 2.

9. The recombinant cell of claim 1 wherein said porcine circovirus comprises a chimeric nucleotide sequence.

10. The recombinant cell of claim 5 wherein the human adenovirus is human adenovirus 5.

* * * * *